(12) United States Patent
Ishida et al.

(10) Patent No.: US 7,538,081 B2
(45) Date of Patent: May 26, 2009

(54) METHOD AND AGENT FOR ENHANCING DIFFUSIVITY AND LONG-LASTING PROPERTY OF FRAGRANCE

(75) Inventors: Kenya Ishida, Kanagawa (JP); Takashi Nishida, Rockleigh, NJ (US); Hiroyuki Matsuda, Kanagawa (JP); Hisao Iwai, Kanagawa (JP); Toshimitsu Hagiwara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 411 days.

(21) Appl. No.: 09/949,718

(22) Filed: Sep. 12, 2001

(65) Prior Publication Data
US 2002/0054893 A1    May 9, 2002

(30) Foreign Application Priority Data
Sep. 12, 2000   (JP)   .......................... P. 2000-275928

(51) Int. Cl.
*A61K 8/00* (2006.01)
(52) U.S. Cl. ....................................... 512/19; 514/613
(58) Field of Classification Search .................. 424/401; 514/613; 512/19
See application file for complete search history.

(56) References Cited

U.S. PATENT DOCUMENTS

| | | | | |
|---|---|---|---|---|
| 4,459,425 A | * | 7/1984 | Amano et al. ................ | 424/56 |
| 5,663,460 A | * | 9/1997 | Yamamoto et al. .......... | 568/829 |
| 5,760,085 A | * | 6/1998 | Beck et al. ................... | 514/613 |

FOREIGN PATENT DOCUMENTS

| | | |
|---|---|---|
| CA | 2361845 A1 | 10/2000 |
| CN | 1252709 A | 5/2000 |
| EP | 0 695 509 A2 | 2/1996 |
| EP | 0 997 144 A1 | 5/2000 |
| GB | 1 315 626 | 5/1973 |
| GB | 1315626 * | 7/1974 |
| JP | 60 025908 | 2/1985 |
| JP | 5-295388 | 11/1993 |
| JP | 7-62383 | 3/1995 |
| JP | 10 194926 | 7/1998 |
| JP | 10-313819 | 12/1998 |
| JP | 3045562 | 3/2000 |
| JP | 2000 239142 | 9/2000 |
| WO | WO 93/00018 | 1/1993 |
| WO | WO 94/08550 A1 | 4/1994 |
| WO | WO 98/47482 A1 | 10/1998 |
| WO | WO 98/47483 A1 | 10/1998 |
| WO | WO 9847483 A1 * | 10/1998 |
| WO | WO 99/13734 A1 | 3/1999 |
| WO | WO 00/62737 A1 | 10/2000 |

OTHER PUBLICATIONS

The Condensed Chemical Dictionary, 1971, (8th ed. by Gessner Hawley), Van Nostrand Reihold Co., p. 566.*
European Search Report.

* cited by examiner

*Primary Examiner*—Gina C. Yu
(74) *Attorney, Agent, or Firm*—Sughrue Mion, PLLC

(57) ABSTRACT

A fragrance composition having an excellent diffusivity and long-lasting property of fragrance and a cosmetic, toiletry, bath composition, food and drink and pharmaceutical having an excellent diffusivity and long-lasting property of fragrance by using a novel fixative. A compound represented by the following general formula (1) is incorporated in a fragrance composition or the foregoing products. The amount of the compound of the general formula (1) to be incorporated in the fragrance composition is preferably from 0.01 to 90% by weight. The amount of the compound of the general formula (1) to be incorporated directly in the foregoing products is preferably from 0.0001 to 2.0 times (by weight) the weight of the aroma composition and/or composition to be incorporated therein. In this arrangement, a fragrance composition or products having an enhanced diffusivity and long-lasting property of fragrance can be obtained without causing any safety problem on human being.

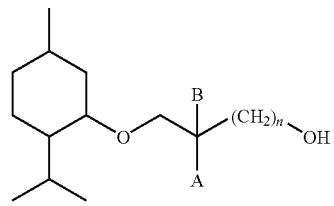

(1)

wherein A represents H or OH group; B represents H or methyl group; and n represents an integer of from 0 to 2.

1 Claim, No Drawings

METHOD AND AGENT FOR ENHANCING DIFFUSIVITY AND LONG-LASTING PROPERTY OF FRAGRANCE

FIELD OF THE INVENTION

The present invention relates to a method for the enhancement of diffusivity and long-lasting property of fragrance, an agent for the enhancement of diffusivity and long-lasting property of fragrance of an aroma component and/or fragrance composition, a fragrance composition having an excellent diffusivity and long-lasting property and a cosmetic, toiletry, bath composition, food and drink and pharmaceutical having an excellent diffusivity and long-lasting property of fragrance comprising these ingredients.

BACKGROUND ART

In order to prepare an excellent fragrance composition by blending aroma materials or blend such a fragrance composition with various products, various fixatives have been hitherto used for the purpose of allowing the fragrance composition and various products to keep diffusivity of desired fragrance and adjusting the fragrance properties and long-lasting property of aroma materials. Known fixatives include various compounds such as dipropylene glycol, triethyl citrate, benzyl benzoate, benzyl salicylate and diethyl phthalate. These compounds have heretofore been incorporated in fragrance compositions or various products. However, mere use of these fixatives is not sufficient for the adjustment of volatility and long-lasting property of aroma components and fragrance compositions. Some of these fixatives have a safety problem. Thus, studies have been made to obtain fixatives having an excellent diffusivity and long-lasting property of fragrance and causing no safety problem. As fixatives having these properties there have recently been proposed p-menthane-3,8-diol (Japanese Patent No. 3,045,562), 2-hydroxymethyl-cycloalkanol derivative (JP-A-5-295388), and specific biphenyl compounds (JP-A-7-62383). (The term "JP-A" as used herein means an "unexamined published Japanese patent application".)

While these prior art references to the results of long-lasting property test on fragrance compositions made organoleptically on blotter, there is no reference to the fixing effect in products (e.g., a cosmetic, toiletry, bath composition, food and drink or pharmaceutical) provided with a fragrance composition containing the foregoing compound as a fixative. It has thus been desired to develop and provide a novel fixative for the purpose of further improving fixing effects in fragrance compositions, expanding the variation of fixatives with respect to fragrance compositions or further enhancing diffusivity and long-lasting property of fragrance in products comprising various fragrance compositions incorporated therein.

An object of the invention is to provide a method which can provide improved diffusivity and long-lasting property of fragrance as compared with a method using conventional known fixatives and which enhance diffusivity and long-lasting property of fragrance without causing any safety problem, an agent for the enhancement of diffusivity and long-lasting property of fragrance of an aroma component and/or fragrance composition to be used in the method, a fragrance composition having excellent diffusivity and long-lasting property of fragrance comprising the agent incorporated therein, and products such as a cosmetic, toiletry, bath composition, food and drink and pharmaceutical having excellent diffusivity and long-lasting property of fragrance comprising these ingredients.

SUMMARY OF THE INVENTION

The inventors made extensive studies for a solution to the foregoing problems with the prior art. As a result, it was found that the incorporation of a compound represented by the following general formula (1) in a fragrance composition, the incorporation of a fragrance composition containing a compound of the general formula (1) in various products, or the incorporation of a compound of the general formula (1) together with a fragrance composition in various products during the preparation of these products makes it possible to obtain a fragrance composition having a remarkably enhanced diffusivity and long-lasting property of fragrance or various products having excellent diffusivity and long-lasting property of fragrance. It was also found that products thus prepared have no safety problems. The present invention has thus been reached.

The present invention has the following aspects.

1. A method for the enhancement of diffusivity and long-lasting property of fragrance, which comprises using a compound represented by the following formula (1):

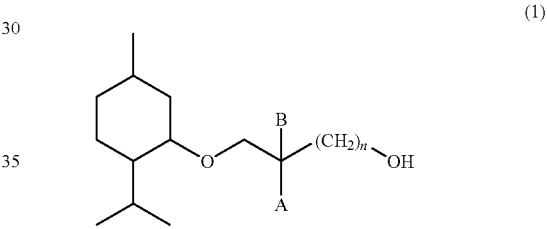

(1)

wherein A represents an H or OH group; B represents an H or methyl group; and n represents an integer of from 0 to 2.

2. A cosmetic which has enhanced diffusivity and long-lasting property of fragrance of an aroma component and/or fragrance composition provided by a method for the enhancement of diffusivity and long-lasting property of fragrance according to 1. above.

3. A toiletry which has enhanced diffusivity and long-lasting property of fragrance of an aroma component and/or fragrance composition provided by a method for the enhancement of diffusivity and long-lasting property of fragrance according to 1. above.

4. A bath composition which has enhanced diffusivity and long-lasting property of fragrance of an aroma component and/or fragrance composition provided by a method for the enhancement of diffusivity and long-lasting property of fragrance according to 1. above.

5. A food or drink which has enhanced diffusivity and long-lasting property of fragrance of an aroma component and/or fragrance composition provided by a method for the enhancement of diffusivity and long-lasting property of fragrance according to 1. above.

6. A pharmaceutical which has enhanced diffusivity and long-lasting property of fragrance of an aroma component and/or fragrance composition provided by a method for the enhancement of diffusivity and long-lasting property of fragrance according to 1. above.

7. A fragrance composition which comprises:
(i) a compound represented by the following formula (1):

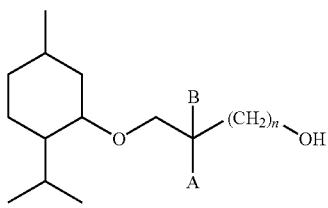

(1)

wherein A represents an H or OH group; B represents an H or methyl group; and n represents an integer of from 0 to 2, and
(ii) an aroma component or a fragrance composition,
wherein the amount of the compound (i) is from 0.01 to 90% by weight based on the total composition, and
the fragrance composition of (ii) has at least one note selected from the group consisting of floral, citrus, fruity, green, mint, herb, and marine.

8. The fragrance composition according to 7. above, wherein said fragrance composition of (ii) has at least one note selected from the group consisting of floral, citrus, and fruity.

9. A fragrance composition which comprises:
(i) a compound represented by the following formula (2):

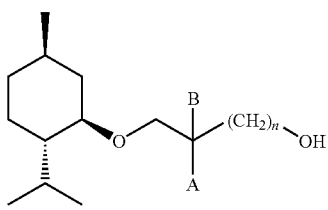

(2)

wherein A represents an H or OH group; B represents an H or methyl group; and n represents an integer of from 0 to 2, and
(ii) an aroma component or a fragrance composition,
wherein the amount of the compound (i) is from 0.01 to 90% by weight based on the total composition, and
the fragrance composition of (ii) has at least one note selected from the group consisting of floral, citrus, fruity, green, mint, herb, and marine.

10. The fragrance composition according to 9. above, wherein said fragrance composition of (ii) has at least one note selected from the group consisting of floral, citrus, and fruity.

11. A cosmetic which comprises:
(i) a compound represented by the following formula (1):

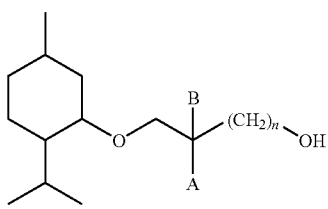

(1)

wherein A represents an H or OH group; B represents an H or methyl group; and n represents an integer of from 0 to 2, and (ii) an aroma component or a fragrance composition,
wherein the concentration of the compound (i) is in the range which does not show a cooling effect, and
the fragrance composition of (ii) has at least one note selected from the group consisting of floral, citrus, fruity, green, mint, herb, and marine.

12. A toiletry which comprises:
(i) a compound represented by the following formula (1):

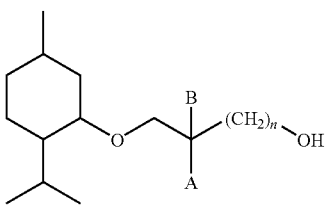

(1)

wherein A represents an H or OH group; B represents an H or methyl group; and n represents an integer of from 0 to 2, and
(ii) an aroma component or a fragrance composition,
wherein the concentration of the compound (i) is in the range which does not show a cooling effect, and the fragrance composition of (ii) has at least one note selected from the group consisting of floral, citrus, fruity, green, mint, herb, and marine.

13. A bath composition which comprises:
(i) a compound represented by the following formula (1):

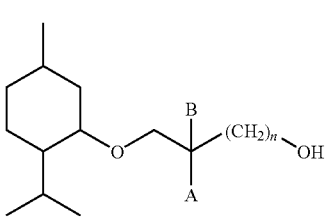

(1)

wherein A represents an H or OH group; B represents an H or methyl group; and n represents an integer of from 0 to 2, and
(ii) an aroma component or a fragrance composition,
wherein the concentration of the compound (i) is in the range which does not show a cooling effect, and
the fragrance composition of (ii) has at least one note selected from the group consisting of floral, citrus, fruity, green, mint, herb, and marine.

14. A food or drink which comprises:
(i) a compound represented by the following formula (1):

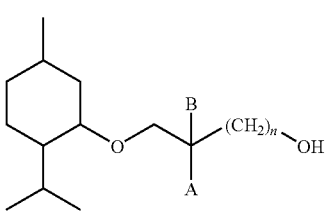

(1)

wherein A represents an H or OH group; B represents an H or methyl group; and n represents an integer of from 0 to 2, and
  (ii) an aroma component or a fragrance composition,
  wherein the concentration of the compound (i) is in the range which does not show a cooling effect, and
  the fragrance composition of (ii) has at least one note selected from the group consisting of floral, citrus, fruity, green, mint, herb, and marine.
  15. A pharmaceutical which comprises:
  (i) a compound represented by the following formula (1):

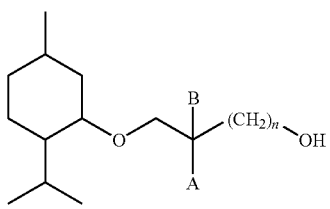

(1)

wherein A represents an H or OH group; B represents an H or methyl group; and n represents an integer of from 0 to 2, and
  (ii) an aroma component or a fragrance composition,
  wherein the concentration of the compound (i) is in the range which does not show a cooling effect, and
  the fragrance composition of (ii) has at least one note selected from the group consisting of floral, citrus, fruity, green, mint, herb, and marine.
  16. A cosmetic which comprises:
  (i) a compound represented by the following formula (2):

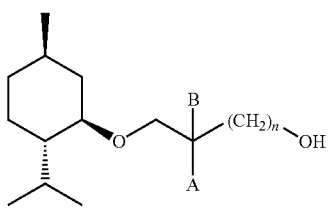

(2)

wherein A represents an H or OH group; B represents an H or methyl group; and n represents an integer of from 0 to 2, and
  (ii) an aroma component or a fragrance composition,
  wherein the concentration of the compound (i) is in the range which does not show a cooling effect, and
  the fragrance composition of (ii) has at least one note selected from the group consisting of floral, citrus, fruity, green, mint, herb, and marine.
  17. A toiletry which comprises:
  (i) a compound represented by the following formula (2):

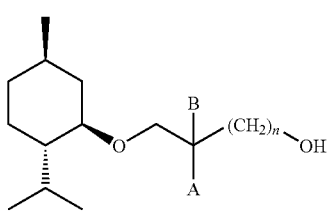

(2)

wherein A represents an H or OH group; B represents an H or methyl group; and n represents an integer of from 0 to 2, and (ii) an aroma component or a fragrance composition,
  wherein the concentration of the compound (i) is in the range which does not show a cooling effect, and
  the fragrance composition of (ii) has at least one A note selected from the group consisting of floral, citrus, fruity, green, mint, herb, and marine.
  18. A bath composition which comprises:
  (i) a compound represented by the following formula (2):

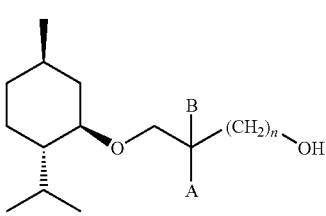

(2)

wherein A represents an H or OH group; B represents an H or methyl group; and n represents an integer of from 0 to 2, and
  (ii) an aroma component or a fragrance composition,
  wherein the concentration of the compound (i) is in the range which does not show a cooling effect, and
  the fragrance composition of (ii) has at least one note selected from the group consisting of floral, citrus, fruity, green, mint, herb, and marine.
  19. A food or drink which comprises:
  (i) a compound represented by the following formula (2):

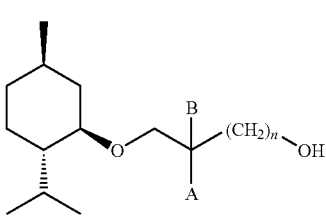

(2)

wherein A represents an H or OH group; B represents an H or methyl group; and n represents an integer of from 0 to 2, and
  (ii) an aroma component or a fragrance composition,
  wherein the concentration of the compound (i) is in the range which does not show a cooling effect, and
  the fragrance composition of (ii) has at least one note selected from the group consisting of floral, citrus, fruity, green, mint, herb, and marine.
  20. A pharmaceutical which comprises:
  (i) a compound represented by the following formula (2):

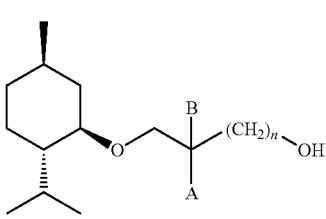

(2)

wherein A represents an H or OH group; B represents an H or methyl group; and n represents an integer of from 0 to 2, and (ii) an aroma component or a fragrance composition, wherein the concentration of the compound (i) is in the range which does not show a cooling effect, and the fragrance composition of (ii) has at least one note selected from the group consisting of floral, citrus, fruity, green, mint, herb, and marine.

DETAILED DESCRIPTION OF THE INVENTION

The term "fragrance" as used herein includes flavors and the term "fragrance composition" as used herein means a mixture of aroma components and includes flavor compositions. Accordingly, the term "fragrance" is synonymous with "flavor and/or fragrance" and the term "fragrance composition" is synonymous with "flavor and/or fragrance composition".

As mentioned above, a compound represented by the foregoing general formula (1) is used in the method for the enhancement of diffusivity and long-lasting property of fragrance according to the invention, the agent for the enhancement of diffusivity and long-lasting property of fragrance of an aroma component and/or fragrance composition according to the invention, the fragrance composition having an excellent diffusivity and long-lasting property of fragrance according to the invention, and the cosmetic, toiletry, bath composition, food and drink and pharmaceutical having an excellent diffusivity and long-lasting property of fragrance comprising these ingredients according to the invention. Examples of the compound represented by the general formula (1) include 2-(menthoxy)ethane-1-ol, 1-(menthoxy)propane-2-ol, 3-(menthoxy)propane-i-ol, 3-(menthoxy)propane-1,2-diol, 2-methyl-3-(menthoxy)propane-1,2-diol, and 4-(menthoxy)butane-1-ol.

A compound represented by the foregoing general formula (2) is preferably used as the compound represented by the general formula (1) to be used in the method for the enhancement of diffusivity and long-lasting property of fragrance according to the invention, the agent for the enhancement of diffusivity and long-lasting property of fragrance of an aroma component and/or fragrance composition according to the invention, the fragrance composition having an excellent diffusivity and long-lasting property of fragrance according to the invention and the cosmetic, toiletry, bath composition, food and drink and pharmaceutical having an excellent diffusivity and long-lasting property of fragrance comprising these ingredients according to the invention. Examples of the compound represented by the general formula (2) include 2-(l-menthoxy)ethane-1-ol, 1-(l-menthoxy)propane-2-ol, 3-(l-menthoxy)propane-1-ol, 3-(l-menthoxy)propane-1,2-diol, 2-methyl-3-(l-menthoxy)propane-1,2-diol, and 4-(l-menthoxy)butane-1-ol.

These compounds may be used singly or in combination of two or more thereof. These compounds are colorless substantially odorless oil-based materials and have an extremely high compatibility with ordinary fragrance compositions.

Particularly preferred among these compounds are 3-(menthoxy)propane-1,2-diol and 3-(l-menthoxy)propane-1,2-diol from the standpoint of long-lasting property in products such as cosmetic, toiletry, bath composition, food and drink and pharmaceutical. It was already known in JP-B-61-48813 (The term "JP-B" as used herein means an "examined Japanese patent application"), JP-A-47-16647, etc. that l-menthoxyether derivatives represented by the general formula (2), particularly 3-(l-menthoxy)propane-1,2-diol, have a cooling effect. In the case where the compound represented by the general formula (1) is a compound having a cooling effect, particularly where the compound represented by the general formula (1) is incorporated in products together with a fragrance composition during the preparation thereof, the diffusivity and long-lasting property of fragrance of the fragrance can be improved even if the compound represented by the general formula (1) is used in an amount less than the value by which the products provided with a fragrance composition are provided with a cooling effect. It is also known that 3-(l-menthoxy)propane-1,2-diol can be applied to a composition for inhibiting inflammation of throat and nose because of its cooling effect (WO 94/08550, WO 98/47483, WO 98/47482). It is further known that a compound represented by the general formula (2) can be incorporated in a food and drink, cosmetic, pharmaceutical or the like, singly or in combination with other compounds, to exert a cooling effect or plasticizing effect (JP-A-10-313819, JP-A-60-25908, JP-A-10-109945). However, there are no reports suggesting that compounds represented by the general formula (1), including those represented by the general formula (2), have an effect of remarkably enhancing diffusivity and long-lasting property of fragrance of fragrance compositions and diffusivity and long-lasting property of fragrance of various products.

The compound represented by the general formula (1) or (2) to be used in the invention is a known compound. The synthesis of the compound represented by the general formula (1) or (2) can be accomplished by utilizing any method disclosed in JP-B-61-48813, British Patent 1,315,626, JP-A-9-217083, etc., which is incorporated by reference herein.

In the invention, the amount of the compound represented by the general formula (1) or (2) to be incorporated in a fragrance composition or product and the method for applying the compound represented by the general formula (1) or (2) to the fragrance composition or product may be optimized depending on the kind and purpose of the fragrance or product in which the compound represented by the general formula (1) or (2) is incorporated. Particularly preferred examples of notes of the fragrance composition to which the agent for the enhancement of diffusivity and long-lasting property of fragrance of an aroma component and/or fragrance composition of the invention is applied include those having at least one note selected from the group consisting of floral, citrus, fruity, green, mint, herb, and marine (e.g., floral citrus green). Preferred notes include floral, citrus and fruity. Particularly preferred examples of floral notes include rose, muguet, lavender, lilac, carnation, and freesia notes.

The amount of the compound represented by the general formula (1) or (2) to be incorporated as an agent for the enhancement of diffusivity and long-lasting property of fragrance of an aroma component and/or fragrance composition when used in a fragrance composition is preferably from 0.01% by weight to 90% by weight, more preferably from 1% by weight to 50% by weight based on the total weight of the fragrance composition. The amount of the fragrance composition having an enhanced diffusivity and long-lasting property of fragrance provided by the addition of the agent to be incorporated in the product is preferably from 0.01 to 50% by weight, particularly from 0.1 to 30% by weight based on the total weight of the product.

On the other hand, the amount of the compound represented by the general formula (1) or (2) to be incorporated directly in various products is arbitrary depending on the form and purpose of the products. In practice, however, it is preferably from 0.0001 to 2.0 times, more preferably from 0.0005 to 1.5 times (by weight) the weight of the aroma composition and/or fragrance composition to be incorporated in the products. Most of the compounds represented by the general formula (2) have a cooling effect when applied to the skin or into the oral cavity. However, even when used in a concentration that gives no cooling effect, the compound of the general formula (2) can sufficiently exert the effect of the invention. For products which are externally applied to skin, scalp or the like, the compound of the general formula (2) can work even when used in an amount of less than 0.001% based on the total weight of the composition.

The compound of the general formula (1) does not show the cooling effect without depending on the concentration. The concentration wherein the compound of the general formula (2) in the products shows no cooling effect differs depending on the forms of the products and the methods for use. In general, in the products for direct use to the skin, scalp, etc. (e.g., the lotions described below, skin cosmetics described below, poultice pharmaceutical, hair cosmetics such as shampoo, rinse, conditioners, hair tonic, hair cream, etc., shaving foam, shaving gel, bath composition, soap, etc.), the concentration wherein the compound of the general formula (2) in the products shows no cooling effect is 0.1% (w/w) or less based on the total composition. In the products which are applied into the oral cavity (e.g., toothpaste, mouthwash, refreshing beverage, gum, candy, ice cream, sherbet, jelly, etc.), the concentration wherein the compound of the general formula (2) in the products shows no cooling effect is 0.001% (w/w) or less based on the total composition.

For the products which are not applied to the skin or scalp or into the oral cavity (e.g., detergent, softener, indoor aromatic, hair bleach, hair color, etc.), the amounts for use are as described above.

The product to which the invention is applied, e.g., cosmetic, toiletry, bath composition, food and drink, pharmaceutical may comprise arbitrary ingredients incorporated therein depending on the purpose besides the fragrance composition having an enhanced diffusivity and long-lasting property of fragrance of the invention or agent for the enhancement of diffusivity and long-lasting property of fragrance of an aroma component and/or fragrance composition of the invention.

The fragrance composition having an enhanced diffusivity and long-lasting property of fragrance of the invention comprises a compound represented by the general formula (1) incorporated therein as an essential ingredient. The fragrance composition having an enhanced diffusivity and long-lasting property of fragrance of the invention may further comprise ketones, aldehydes, esters, alcohols, ethers, terpenes, natural essential oils, synthetic musk or common materials constituting fragrance composition incorporated therein as necessary. The incorporation of the compound represented by the general formula (1) in the fragrance composition as an agent for the enhancement of diffusivity and long-lasting property of fragrance of an aroma component and/or fragrance composition makes it possible to remarkably enhance diffusivity and long-lasting property of fragrance, i.e., fragrance properties and fixation of the fragrance composition. Further, the incorporation of the fragrance composition having an enhanced diffusivity and long-lasting property of fragrance thus obtained during the preparation of products makes it possible to obtain products having improved diffusivity and long-lasting property of fragrance as compared with products comprising a compound represented by the general formula (1) directly incorporated therein.

In addition to the essential components of the present invention as described above, each of the cosmetic, toiletry, bath composition, food and drink and pharmaceutical may comprises a carrier, a diluent, etc. which is acceptable as a cosmetic, toiletry, bath composition, food and drink or pharmaceutical.

Examples of the cosmetic, toiletry, bath composition, food and drink and pharmaceutical as used in the invention include various lotions such as beauty wash, body lotion, after shave lotion and hair growth lotion, skin cosmetics such as milky lotion and cream, poultice pharmaceutical, pasting, hair cosmetics such as shampoo, rinse, conditioners, hair tonic and hair cream, perfume, Cologne, bath composition, soap, shaving foam, shaving gel, detergent, softener, indoor aromatic, toothpaste, mouthwash, ointment, refreshing beverage, gum, candy, ice cream, sherbet, jelly, and carbonated water.

The parts, ratios, percentages, or the like used in this specification are by weight.

The present invention will be further described in the following Examples and Comparative Examples, but the present invention should not be construed as being limited thereto.

EXAMPLE 1 AND COMPARATIVE EXAMPLES 1 TO 3

Test on Effect of Diffusivity and Long-lasting Property of Fragrance of Fragrance Composition Fragrance compositions of Example 1 and Comparative Examples 1 to 3 having the formulation set forth in Table 1 were prepared according to an ordinary method. These fragrance compositions were then evaluated for diffusivity and long-lasting property of fragrance in the following manner. For the evaluation of long-lasting property of fragrance, fragrance substantivity test was carried out. (Test method for diffusivity and substantivity of fragrance of fragrance composition)

10.0 mg of a fragrance composition prepared was measured out on a filter paper laid on the bottom of a wide-mouthed bottle having a diameter of 40 mm and a height of 50 mm. The bottle was closed, and then allowed to stand for 30 minutes to prepare an evaluation sample. When the bottle was opened, the sample was immediately evaluated organoleptically for fragrance diffusivity. In this open system, the sample was then allowed to stand for about 5 hours. The sample was then organoleptically evaluated for fragrance substantivity. The evaluation of these properties was made three times by 11 fragrance experts who had experienced over 5 years (33 experts in total). The evaluation was conducted relative to Comparative Example 3.

TABLE 1

| Ingredient | Example 1 | Comparative Example 1 | Comparative Example 2 | Comparative Example 3 |
|---|---|---|---|---|
| Aldehyde $C_{10}$ | 2.0 (g) | 2.0 (g) | 2.0 (g) | 2.0 (g) |
| Citral | 5.0 | 5.0 | 5.0 | 5.0 |
| Dihydromyrcenol | 5.0 | 5.0 | 5.0 | 5.0 |
| Hexamethyl hexahydrocyclopentabenzopyran | 15.0 | 15.0 | 15.0 | 15.0 |
| Geranyl nitrile | 3.0 | 3.0 | 3.0 | 3.0 |
| Hexylcinnamic aldehyde | 10.0 | 10.0 | 10.0 | 10.0 |
| Lemon oil | 30.0 | 30.0 | 30.0 | 30.0 |
| Linanool | 10.0 | 10.0 | 10.0 | 10.0 |
| Orange oil | 15.0 | 15.0 | 15.0 | 15.0 |
| Terpineol | 5.0 | 5.0 | 5.0 | 5.0 |
| 3-(l-Menthoxy)propane-1,2-diol | 10.0 | — | — | — |

TABLE 1-continued

| Ingredient | Example 1 | Comparative Example 1 | Comparative Example 2 | Comparative Example 3 |
|---|---|---|---|---|
| Dipropylene glycol | — | 10.0 | — | — |
| Triethyl citrate | — | — | 10.0 | — |

(1) Results of Fragrance Diffusivity Test

The number of experts which felt most fragrance diffusivity with respect to Comparative Example 3 is set forth in Table 2 below.

TABLE 2

|  | Example 1 | Comparative Example 1 | Comparative Example 2 | No difference felt |
|---|---|---|---|---|
| Number of experts | 13 | 8 | 6 | 6 |

(2) Results of Fragrance Substantivity Test

The number of experts which felt most fragrance substantivity with respect to Comparative Example 3 is set forth in Table 3 below.

TABLE 3

|  | Example 1 | Comparative Example 1 | Comparative Example 2 | No difference felt |
|---|---|---|---|---|
| Number of experts | 26 | 2 | 3 | 2 |

As can be seen in Tables 2 and 3 above, the compound of the invention exhibited excellent results in fragrance diffusivity from the foregoing fragrance ingredient and fragrance substantivity of the fragrance composition as compared with known fixative.

EXAMPLE 2 AND COMPARATIVE EXAMPLE 4

Effect Test on Bath Composition

Bath compositions of Example 2 and Comparative Example 4 provided with 1.0% of the fragrance composition of Example 1 and Comparative Example 1, respectively, were each prepared in an amount of 100 g according to the formulation set forth in Table 4 below. 20 g of each of these bath compositions was then dissolved in 180 l of hot water having a temperature of from 40° C. to 42° C. These solutions thus prepared were immediately evaluated comparatively for fragrance intensity by the experts. These solutions were also evaluated for fragrance intensity after 30 minutes. The evaluation was made three times by 11 fragrance experts who had experienced over 5 years (33 experts in total). The evaluation was conducted relative to Comparative Example 4.

TABLE 4

| Ingredient | Example 2 | Comparative Example 4 |
|---|---|---|
| Anhydrous sodium sulfate | 68.45 (g) | 68.45 (g) |
| Sodium hydrogencarbonate | 30.00 | 30.00 |
| Silicic anhydride | 0.50 | 0.50 |
| Colouring | 0.05 | 0.05 |
| Fragrance of Example 1 | 1.00 | — |
| Fragrance of Comparative Example 1 | — | 1.00 |
| Total | 100 | 100 |

(1) Results of Fragrance Diffusivity Test

For the comparison of the bath compositions of Example 2 and Comparative Example 4, the number of experts who felt that the bath composition of Example 2 has a high fragrance diffusivity, the number of experts who felt that the bath composition of Comparative Example 4 has a high fragrance diffusivity, and the number of experts who felt no difference between the two bath compositions are set forth in Table 5 below.

TABLE 5

|  | Example 2 | Comparative Example 4 | No difference felt |
|---|---|---|---|
| Number of experts | 20 | 8 | 5 |

(2) Results of Fragrance Substantivity Test

For the comparison of the bath compositions of Example 2 and Comparative Example 4, the number of experts who felt that the bath composition of Example 2 has a high fragrance substantivity, the number of experts who felt that the bath composition of Comparative Example 4 has a high fragrance substantivity, and the number of experts who felt no difference between the two bath compositions are set forth in Table 6 below.

TABLE 6

|  | Example 2 | Comparative Example 4 | No difference felt |
|---|---|---|---|
| Number of experts | 21 | 5 | 7 |

As can be seen in Tables 5 and 6, the bath compositions comprising fragrance compositions of the invention exhibited excellent results in both diffusivity and long-lasting property of fragrance as compared with the bath composition containing dipropylene glycol.

EXAMPLE 3 AND COMPARATIVE EXAMPLE 5

Effect Test on Bath Composition

Bath compositions of Example 3 and Comparative Example 5 were each prepared in an amount of 100 g according to the formulation set forth in Table 7 below. 20 g of each of these bath compositions was then dissolved in 180 l of hot water having a temperature of from 40° C. to 42° C. These solutions thus prepared were immediately evaluated comparatively for fragrance intensity by the experts in the same manner as in Example 2.

TABLE 7

| Ingredient | Example 3 | Comparative Example 5 |
|---|---|---|
| Anhydrous sodium sulfate | 68.45 (g) | 68.45 (g) |
| Sodium hydrogencarbonate | 30.00 | 30.00 |
| Silicic anhydride | 0.50 | 0.50 |
| Colouring | 0.05 | 0.05 |
| Fragrance composition comprising 3-(l-menthoxy)propane-1,2-diol and Type SP-0298 jasmine note fragrance composition (produced by TAKASAGO INTERNATIONAL CORP.) at a weight ratio of 1:9 | 1.00 | — |
| Type SP-0298 jasmine note fragrance composition (produced by TAKASAGO INTERNATIONAL CORP.) | — | 1.00 |

(1) Results of Fragrance Diffusivity Test

The number of experts who felt that the bath compositions of Example 3 and Comparative Example 5 have a high fragrance diffusivity, respectively, is set forth in Table 8 below.

TABLE 8

|  | Example 3 | Comparative Example 5 | No difference felt |
|---|---|---|---|
| Number of experts | 17 | 10 | 6 |

(2) Results of Fragrance Substantivity Test

The number of experts who felt that the bath composition of Example 3 and Comparative Example 5 have a high fragrance substantivity, respectively, is set forth in Table 9 below.

TABLE 9

|  | Example 3 | Comparative Example 5 | No difference felt |
|---|---|---|---|
| Number of experts | 13 | 9 | 11 |

As can be seen in Tables 8 and 9, the bath compositions comprising fragrance composition of the invention exhibited excellent results in both diffusivity and long-lasting property of fragrance as compared with the bath composition comprising a fragrance composition having no 3-(l-menthoxy)propane-1,2-diol.

PREPARATION OF EXAMPLE 4 AND COMPARATIVE EXAMPLE 6

Preparation of Fragrance Composition

Fragrance compositions of Example 4 and Comparative Example 6 were prepared according to the formulation set forth in Table 10 below.

TABLE 10

| Ingredient | Example 4 | Comparative Example 6 |
|---|---|---|
| Bergamot oil | 11.0 (g) | 11.0 (g) |
| Cis-3-hexenyl salicylate | 2.0 | 2.0 |
| Dihydromircenol | 10.0 | 10.0 |

TABLE 10-continued

| Ingredient | Example 4 | Comparative Example 6 |
|---|---|---|
| Ethyl linalool | 2.0 | 2.0 |
| Methyl dihydrojasmonate | 25.0 | 25.0 |
| Helional | 3.0 | 3.0 |
| Lemon oil | 5.0 | 5.0 |
| Linalyl acetate | 16.0 | 16.0 |
| Ethylene brassylate | 18.0 | 18.0 |
| Phenyl ethyl alcohol | 8.0 | 8.0 |
| 3-(l-Menthoxy)propane-1,2-diol | 5.0 | — |
| p-Menthane-3,8-diol | — | 5.0 |
| Total | 100 | 100 |

EXAMPLE 5 AND COMPARATIVE EXAMPLE 7

Effect Test on Eau De Cologne

Eau De Colognes (95% ethanol solution) provided with 5% of fragrance compositions of Example 4 and Comparative Example 6 were prepared each in an amount of 100 g. These Eau De Colognes were then sprayed onto the inner side of right and left forearms of fragrance experts through an atomizer. The Eau De Colognes thus sprayed were each immediately evaluated for fragrance diffusivity. After about 4 hours, these Eau De Colognes were evaluated for fragrance substantivity. The evaluation was made by 13 fragrance experts who had experienced over 5 years.

(1) Results of Fragrance Diffusivity Test

For the comparison of the Eau De Colognes of Example 5 and Comparative Example 7, the number of experts who felt that the Eau De Cologne of Example 5 has a high fragrance diffusivity, the number of experts who felt that the Eau De Cologne of Comparative Example 7 has a high fragrance diffusivity, and the number of experts who felt no difference between the two Eau De Colognes are set forth in Table 11 below.

TABLE 11

|  | Example 5 | Comparative Example 7 | No difference felt |
|---|---|---|---|
| Number of experts | 6 | 3 | 4 |

(2) Results of Fragrance Substantivity Test

For the comparison of the Eau De Colognes of Example 5 and Comparative Example 7, the number of experts who felt that the Eau De Cologne of Example 5 has a high fragrance substantivity, the number of experts who felt that the Eau De Cologne of Comparative Example 7 has a high fragrance substantivity, and the number of experts who felt no difference between the two bath compositions are set forth in Table 12 below.

TABLE 12

|  | Example 5 | Comparative Example 7 | No difference felt |
|---|---|---|---|
| Number of experts | 9 | 3 | 1 |

As can be seen in Tables 11 and 12, the Eau De Cologne comprising fragrance composition of the invention exhibited particularly excellent results especially in fragrance substantivity as compared with the Eau De Cologne comprising p-menthane-3,8-diol.

EXAMPLE 6 AND COMPARATIVE EXAMPLE 8

Preparation of Fragrance

Fragrance compositions of Example 6 and Comparative Example 8 were prepared according to the formulation set forth in Table 13 below.

TABLE 13

| Ingredient | Example 6 | Comparative Example 8 |
| --- | --- | --- |
| Apple base | 10.0(g) | 10.0(g) |
| Bergamot oil | 16.0 | 16.0 |
| Ethyl acetoacetate | 5.0 | 5.0 |
| Methyl dihydrojasmonate | 25.0 | 25.0 |
| Laurinal | 3.0 | 3.0 |
| Levosandol ® | 4.0 | 4.0 |
| Orange oil | 8.0 | 8.0 |
| 10-Oxa-16-hexadecanolide | 10.0 | 10.0 |
| Phenoxanol | 6.0 | 6.0 |
| Styrallyl acetate | 3.0 | 3.0 |
| Ethyl 2,2,6-trimethylcyclohexane carboxylate | 10.0 | 10.0 |
| 3-(l-Menthoxy)propane-1,2-diol | 20.0 | — |
| Dipropylene glycol | — | 20.0 |

EXAMPLE 7 AND COMPARATIVE EXAMPLE 9

Effect Test on Shampoo

Shampoos of Example 7 and Comparative Example 9 provided with 0.5% of fragrance compositions of Example 6 and Comparative Example 8 were prepared each in an amount of 100 g according to the formulation set forth in Table 14 below. The shampoos thus obtained were each then evaluated for diffusivity and long-lasting property of fragrance in the following manner.

(Evaluation Method)

5 g of a tress of hair piece (human hair) was treated with 2.5 g of the shampoo and 5 ml of hot water (40° C.) for 1 minute, rinsed with 1,000 ml of hot water (40° C.), dried over a towel, and then fixed to and allowed to stand on an aluminum foil to prepare an evaluation sample. Shortly after fixed, the sample was then evaluated for fragrance diffusivity. After about 5 hours, the sample was then evaluated for fragrance substantivity. The evaluation was made three times by 10 fragrance experts who had experienced over 5 years (30 experts in total).

TABLE 14

| Ingredient | Weight (g) |
| --- | --- |
| Sodium polyoxyethylenelaurylethersulfate | 14.00 |
| Amidepropylbetain laurate | 4.00 |
| Diethanolamide of coconut oil fatty acid | 3.00 |
| Cationated cellulose | 0.50 |
| Ethylene glycol distearate | 1.00 |
| Paraoxybenzoic acid ester | 0.25 |

TABLE 14-continued

| Ingredient | Weight (g) |
| --- | --- |
| Citric acid | Proper amount |
| Fragrance composition | 0.50 |
| Purified water | Balance |
| Total | 100 |

(1) Results of Fragrance Diffusivity Test on Shampoo

For the comparison of the shampoos of Example 7 and Comparative Example 9, the number of experts who felt that the shampoo of Example 7 has a high fragrance diffusivity, the number of experts who felt that the shampoo of Comparative Example 9 has a high fragrance diffusivity, and the number of experts who felt no difference between the two bath compositions are set forth in Table 15 below.

TABLE 15

| | Example 7 | Comparative Example 9 | No difference felt |
| --- | --- | --- | --- |
| Number of experts | 13 | 9 | 8 |

(2) Results of Fragrance Substantivity Test on Shampoo

For the comparison of the shampoos of Example 7 and Comparative Example 9, the number of experts who felt that the shampoo of Example 7 has a high fragrance substantivity, the number of experts who felt that the bath composition of Comparative Example 9 has a high fragrance substantivity, and the number of experts who felt no difference between the two shampoos are set forth in Table 16 below.

TABLE 16

| | Example 7 | Comparative Example 9 | No difference felt |
| --- | --- | --- | --- |
| Number of experts | 26 | 3 | 1 |

As can be seen in Tables 15 and 16 above, the shampoo comprising a fragrance composition of the invention exhibited excellent results in both diffusivity and long-lasting property of fragrance, particularly in fragrance substantivity.

EXAMPLE 8 AND COMPARATIVE EXAMPLE 10

Effect Test on Conditioner

Conditioners of Example 8 and Comparative Example 10 provided with 0.5% of fragrance compositions of Example 6 and Comparative Example 8 were prepared each in an amount of 100 g according to the formulation set forth in Table 17 below. The conditioners thus obtained were each then evaluated in the following manner.

(Evaluation Method)

5 g of a tress of hair piece was treated with 5.0 g of the conditioner and 5 ml of hot water (40° C.) for 1 minute, rinsed with 1,000 ml of hot water (40° C.), dried over a towel, and then fixed to and allowed to stand on an aluminum foil to prepare an evaluation sample. The sample was then evaluated for diffusivity and long-lasting property of fragrance in the same manner as shampoo.

TABLE 17

| Ingredient | Weight (g) |
|---|---|
| Stearyl trimethyl ammonium chloride | 0.50 |
| Distearyl dimethyl ammonium chloride | 1.50 |
| Jojoba oil | 2.50 |
| Cetanol | 4.50 |
| Liquid lanolin | 2.00 |
| Polyoxyethylene stearyl ether | 1.50 |
| Concentrated glycerin | 7.00 |
| Paraoxybenzoic acid ester | 0.25 |
| Sodium hydroxide | Proper amount |
| Citric acid | Proper amount |
| Fragrance composition | 0.50 |
| Purified water | Balance |
| Total | 100 |

(1) Results of Fragrance Diffusivity Test on Conditioner

For the comparison of the conditioners of Example 8 and Comparative Example 10, the number of experts who felt that the conditioner of Example 8 has a high fragrance diffusivity, the number of experts who felt that the conditioner of Comparative Example 10 has a high fragrance diffusivity, and the number of experts who felt no difference between the two conditioners are set forth in Table 18 below.

TABLE 18

|  | Example 8 | Comparative Example 10 | No difference felt |
|---|---|---|---|
| Number of experts | 20 | 8 | 2 |

(2) Results of Fragrance Substantivity Test on Conditioner

For the comparison of the bath compositions of Example 8 and Comparative Example 10, the number of experts who felt that the bath composition of Example 8 has a high fragrance substantivity, the number of experts who felt that the bath composition of Comparative Example 10 has a high fragrance substantivity, and the number of experts who felt no difference between the two conditioners are set forth in Table 19 below.

TABLE 19

|  | Example 8 | Comparative Example 10 | No difference felt |
|---|---|---|---|
| Number of experts | 21 | 5 | 4 |

As can be seen in Tables 18 and 19, the conditioner comprising the fragrance composition of the invention exhibited remarkable results in both diffusivity and long-lasting property of fragrance.

EXAMPLES 9 And 10; COMPARATIVE EXAMPLE 11

Effect Test 2 on Shampoo

Shampoos of Examples 9 and 10 and Comparative Example 11 provided with 0.3% of floral fruity green type fragrance composition (TSP-3055, produced by TAKASAGO INTERNATIONAL CORP.) were prepared each in an amount of 100 g in a conventional manner according to the formulation set forth in Table 20 below.

TABLE 20

| Ingredient | Example 9 | Example 10 | Comparative Example 11 |
|---|---|---|---|
| Sodium polyoxyethylenelaurylether sulfate | 14.00(g) | 14.00(g) | 14.00(g) |
| Amidepropylbetain laurate | 4.00 | 4.00 | 4.00 |
| DiethanolaxnAde of coconut oil fatty acid | 3.00 | 3.00 | 3.00 |
| Cationated cellulose | 0.50 | 0.50 | 0.50 |
| Ethylene glycol distearate | 1.00 | 1.00 | 1.00 |
| Paraoxybenzoic acid ester | 0.25 | 0.25 | 0.25 |
| Citric acid | Proper amount | Proper amount | Proper amount |
| 3-(l-Menthoxy)propane-1,2-diol | — | 0.09 | — |
| Fragrance composition (TSP-3055) | — | 0.30 | 0.30 |
| Fragrance composition comprising 3-(l-menthoxy) propane-1,2-diol and TSP-3055 at a weight ratio of 23:77 | 0.39 | — | — |
| Purified water | Balance | Balance | Balance |
| Total | 100 | 100 | 100 |

These shampoos were each then evaluated for diffusivity and long-lasting property of fragrance in the same manner as in Example 7.

(1) Results of Fragrance Diffusivity Test on Shampoo

The number of experts who felt that the shampoos of Examples 9 and 10 and Comparative Example 11 have highest fragrance diffusivity, respectively, is set forth in Table 21 below.

TABLE 21

|  | Example 9 | Example 10 | Comparative Example 11 |
|---|---|---|---|
| Number of experts | 16 | 10 | 4 |

(2) Results of Fragrance Substantivity Test on Shampoo

The number of experts who felt that the shampoos of Examples 9 and 10 and Comparative Example 11 have highest fragrance substantivity, respectively, is set forth in Table 22 below.

TABLE 22

|  | Example 9 | Example 10 | Comparative Example 11 |
|---|---|---|---|
| Number of experts | 23 | 5 | 2 |

As can be seen in Tables 21 and 22 above, the shampoos comprising a fragrance composition of the invention containing 3-(l-menthoxy)propane-1,2-diol and the shampoos to which 3-(l-menthoxy)propane-1,2-diol had been added together with fragrance compositions during preparation exhibited excellent results in both diffusivity and long-lasting property of fragrance as compared with those free of 3-(l-menthoxy)propane-1,2-diol. In particular, the shampoos comprising a fragrance composition of the invention containing 3-(l-menthoxy)propane-1,2-diol exhibited remarkable results in fragrance substantivity.

EXAMPLES 11 AND 12 AND COMPARATIVE EXAMPLE 12

Effect Test 2 on Conditioner

Conditioners of Examples 11 and 12 and Comparative Example 12 provided with 0.3% of floral fruity green type fragrance composition (TSP-3055, produced by TAKASAGO INTERNATIONAL CORP.) were prepared each in an amount of 100 g in a conventional manner according to the formulation set forth in Table 23 below.

TABLE 23

| Ingredient | Example 11 | Example 12 | Comparative Example 12 |
|---|---|---|---|
| Stearyl trimethyl ammonium chloride | 0.50 (g) | 0.50 (g) | 0.50 (g) |
| Distearyl dimethyl animonium chloride | 1.50 | 1.50 | 1.50 |
| Jojoba oil | 2.50 | 2.50 | 2.50 |
| Cetanol | 4.50 | 4.50 | 4.50 |
| Liquid lanolin | 2.00 | 2.00 | 2.00 |
| Polyoxyethylene stearyl ether | 1.50 | 1.50 | 1.50 |
| Concentrated glycerin | 7.00 | 7.00 | 7.00 |
| Paraoxybenzoic acid ester | 0.25 | 0.25 | 0.25 |
| Sodium hydroxide | Proper amount | Proper amount | Proper amount |
| Citric acid | Proper amount | Proper amount | Proper amount |
| 3-(l-Menthoxy)propane-1,2-diol | — | 0.09 | — |
| Fragrance composition (TSP-3055) | — | 0.30 | 0.30 |
| Fragrance composition having 3-(l-Menthoxy)propane-1,2-diol and TSP-3055 at a mixing ratio of 23:77 by weight | 0.39 | — | — |
| Purified water | Balance | Balance | Balance |
| Total | 100 | 100 | 100 |

These conditioners were each then evaluated for fragrance in the same manner as in Example 8.

(1) Results of Fragrance Substantivity Test on Conditioner

The number of experts who felt that the conditioners of Examples 11 and 12 and Comparative Example 12 have highest fragrance substantivity, respectively, is set forth in Table 24 below.

TABLE 24

|  | Example 11 | Example 12 | Comparative Example 12 |
|---|---|---|---|
| Number of experts | 20 | 7 | 3 |

As can be seen in Table 24 above, the conditioners comprising a fragrance composition of the invention containing 3-(l-menthoxy)propane-1,2-diol (Example 11) and the conditioners to which 3-(l-menthoxy)propane-1,2-diol had been added together with fragrance compositions during preparation exhibited excellent results in fragrance substantivity (Example 12) as compared with those free of 3-(l-menthoxy) propane-1,2-diol (Comparative Example 12). In particular, the conditioners comprising a fragrance composition of the invention containing 3-(l-menthoxy)propane-1,2-diol (Example 11) exhibited remarkable results in fragrance substantivity.

EXAMPLE 13

Preparation of Emollient Cream 100 g of an emollient cream was prepared in a conventional manner according to the formulation set forth in Table 25 below.

TABLE 25

| Ingredient | Weight (g) |
|---|---|
| Hardened oil | 6.00 |
| Stearic acid | 3.00 |
| Cetanol | 4.00 |
| Squalane | 2.00 |
| Neopentyl glycol dicaprinate | 8.00 |
| Polyoxyethylene sorbitan monostearate (20E.O.) | 4.00 |
| Lipophilic glycerin monostearate | 2.30 |
| Stearoyl-N-methyltaurin sodium | 1.70 |
| 1,3-Butylene glycol | 7.00 |
| Concentrated glycerin | 3.00 |
| Paraoxybenzoic acid ester | 0.25 |
| Floral powdery fragrance composition BF-6370-C (produced by TAKASAGO INTERNATIONAL CORP.) containing 10% of 4-(l-menthoxy)butane-1-ol | 0.05 |
| Vanillyl butyl ether | 0.01 |
| Purified water | Balance |
| Total | 100 |

EXAMPLE 14

Preparation of Emollient Cream 100 g of an emollient cream was prepared in a conventional manner according to the formulation set forth in Table 26 below.

TABLE 26

| Ingredient | Weight (g) |
|---|---|
| Stearic acid | 1.00 |
| Cholesteryl isostearate | 2.00 |
| Jojoba oil | 4.00 |
| Squalane | 8.00 |
| Sorbitan sesquioleate | 0.80 |
| Polyoxyethylene sorbitan monostearate (20E.O.) | 1.20 |
| 1,3-Butylene glycol | 5.00 |
| Paraoxybenzoic acid ester | 0.25 |
| L-arginine | 0.40 |
| Carboxyvinyl polymer | 0.20 |
| Floral powdery fragrance composition BF-6372 (produced by TAKASAGO INTERNATIONAL CORP.) containing 5% of 3-(l-menthoxy)propane-1-ol | 0.10 |
| l-Menthol | 0.20 |
| Purified water | Balance |
| Total | 100 |

EXAMPLE 15

Preparation of Hair Rinse 100 g of a hair rinse was prepared in a conventional manner according to the formulation set forth in Table 27 below.

TABLE 27

| Ingredient | Weight (g) |
| --- | --- |
| Stearyl trimethyl ammonium chloride | 1.00 |
| Cetanol | 3.00 |
| Methyl polysiloxane | 1.00 |
| Polyoxyethylene stearyl ether | 1.00 |
| Propylene glycol | 5.00 |
| Paraoxybenzoic acid ester | 0.25 |
| Sodium hydroxide | Proper amount |
| Citric acid | Proper amount |
| Floral fruity marine note fragrance composition BF-6908 (produced by TAKASAGO INTERNATIONAL CORP.) containing 5% of 2-(menthoxy)ethane-1-ol | 0.50 |
| l-Menthol | 0.20 |
| Purified water | Balance |
| Total | 100 |

EXAMPLE 16

Preparation of Hair Tonic 100 g of a hair tonic was prepared in a conventional manner according to the formulation set forth in Table 28 below.

TABLE 28

| Ingredient | Weight (g) |
| --- | --- |
| Extract of Swertia japonica | 2.00 |
| l-Menthol | 0.10 |
| Hinokitiol | 0.01 |
| Herbal green fragrance composition BF-6167 (produced by TAKASAGO INTERNATIONAL CORP.) containing 20% of 3-(l-menthoxy) propane-1,2-diol | 0.20 |
| Paraoxybenzoic acid ester | 0.20 |
| Polyoxyethylene hardened castor oil | 0.50 |
| Purified water | Balance |
| total | 100 |

EXAMPLE 17

Preparation of Deodorant Powder Spray 100 g of a deodorant powder spray was prepared in a conventional manner according to the formulation set forth in Table 29 below.

TABLE 29

| Ingredient | Weight (g) |
| --- | --- |
| Chlorohydroxyaluminum | 1.00 |
| Silicic anhydride | 1.00 |
| Isopropyl myristinate | 2.00 |
| Octamethyl cyclotetrasiloxane | 2.00 |
| Trichlosane | 0.02 |
| Sorbitan sesquioleate | 0.10 |
| l-Menthol | 0.30 |
| 3-(l-Menthoxy)propane-1,2-diol | 1.50 |
| Vanillyl butyl ether | 0.05 |
| Citrus floral note fragrance composition BC-6021 (produced by TAKASAGO INTERNATIONAL CORP.) | 0.30 |

TABLE 29-continued

| Ingredient | Weight (g) |
| --- | --- |
| containing 20% of 3-(l-menthoxy)propane-1,2-diol | |
| 95% Ethanol | 3.33 |
| LPG | Balance |
| Total | 100 |

EXAMPLE 18

Preparation of Liquid Bath Composition 100 g of a liquid bath composition was prepared in a conventional manner according to the formulation set forth in Table 30 below.

TABLE 30

| Ingredient | Weight (g) |
| --- | --- |
| Dipropylene glycol | 50.00 |
| 1,3-Butylene glycol | 10.00 |
| Paraoxybenzoic acid ester | 0.20 |
| l-Menthol | 0.30 |
| Lemon fragrance note composition BF-6032 (produced by TAKASAGO INTERNATIONAL CORP.) containing 10% of 2-methyl-3-(l-menthoxy)propane-1,2-diol | 1.00 |
| Purified water | Balance |
| Total | 100 |

EXAMPLE 19

Preparation of Gum 100 g of a gum was prepared in a conventional manner according to the formulation set forth in Table 13 below.

TABLE 31

| Ingredient | Weight (g) |
| --- | --- |
| Mint flavor containing 20% of 3-(l-menthoxy)propane-1,2-diol | 1.0 |
| Thick malt syrup | 13.0 |
| Gum resin | 20.0 |
| Powder sugar | Balance |
| Total | 100 |

EXAMPLE 20 AND COMPARATIVE EXAMPLE 13

Preparation of and Effect Test on Toothpaste

Toothpastes of Example 20 and Comparative Example 13 were prepared each in an amount of 100 g in a conventional manner according to the formulation set forth in Table 32 below.

TABLE 32

| Ingredient | Example 20 | Comparative Example 13 |
|---|---|---|
| l-Menthol | 0.5 | 0.5 |
| Calcium hydrogenphosphate (dihydrate) | 50.0 | 50.0 |
| Glycerin | 25.0 | 25.0 |
| Sodium laurylsulfate | 1.4 | 1.4 |
| Carboxymethyl cellulose sodium | 1.5 | 1.5 |
| Saccharin sodium | 0.2 | 0.2 |
| Sodium benzoate | 0.1 | 0.1 |
| Fragrance composition having 3-(menthoxy)propane-1,2-diol and strawberry type flavor ZX-3687 (produced by TAKASAGO INTERNATIONAL CORP.) at a mixing ratio of 3:7 by weight | 1.0 | — |
| Strawberry type flavor ZX-3687 (produced by TAKASAGO INTERNATIONAL CORP.) | — | 0.7 |
| Purified water | Balance | Balance |
| Total | 100 | 100 |

(Evaluation Method)

8 fragrance experts who had experienced over 5 years brushed their teeth with 1.0 g of the toothpaste for 2 minutes, and then rinsed their teeth with 30 ml of water (0 minute). The fragrance intensity was then evaluated at various time points according to the following five-stage criterion. The measurements made by the eight experts were then averaged to make evaluation.

Evaluation point 5: Felt very strongly;
    4: Felt strongly;
    3: Felt moderately;
    2: Felt weakly;
    1: Felt slightly:
    0: Felt nothing

TABLE 33

| | 0 min. | 5 min. | 10 min. | 15 min. | 30 min. |
|---|---|---|---|---|---|
| Example 20 | 4.8 | 3.5 | 2.8 | 2.4 | 1.5 |
| Comparative Example 13 | 3.9 | 2.8 | 2.1 | 1.5 | 0.6 |

As seen in Table 33 above, the toothpaste comprising the fragrance composition of the invention exhibited excellent results in diffusivity and long-lasting property of fragrance.

EXAMPLE 21

Preparation of Carbonated Drink 100 g of a carbonated drink was prepared in a conventional manner according to the formulation set forth in Table 34 below.

TABLE 34

| Ingredient | Weight (g) |
|---|---|
| Concentrated lemon juice | 0.9 |
| Liquid sugar (fruit sugar: glucose) | 25.8 |
| Lemon flavor containing 5% of 2-methyl-3-(l-menthoxy)propane-1,2-diol | 0.2 |
| Vanillyl-n-butyl ether | 0.0001 |

TABLE 34-continued

| Ingredient | Weight (g) |
|---|---|
| Purified water | 40.0 |
| Carbonated water | Balance |
| Total | 100 |

EXAMPLE 22

Preparation of Mouthwash 100 g of a mouthwash was prepared in a conventional manner according to the formulation set forth in Table 35 below.

TABLE 35

| Ingredient | Weight (g) |
|---|---|
| Ethanol | 12.50 |
| Sodium laurylsulfate | 1.25 |
| Glycerin | 10.00 |
| l-Menthol | 0.10 |
| Saccharin | 0.001 |
| Dye | 0.003 |
| Mint flavor containing 30% of 2-methyl-3-(l-menthoxy)propane-1,2-diol | 0.05 |
| Purified water | Balance |
| Total | 100 |

All the emollient cream, emollient milk, hair rinse, hair tonic, deodorant powder spray, liquid bath composition, gum, toothpaste, carbonated drink and mouthwash described in Examples 13 to 22 exhibited good results in diffusivity and long-lasting property of fragrance.

As mentioned in detail above, in accordance with the present invention, the incorporation of a compound represented by the foregoing general formula (1) in a fragrance composition in an amount of from 0.1 to 90% by weight makes it possible to exert an effect of remarkably enhancing diffusivity and long-lasting property of fragrance of an ordinary fragrance without causing any safety problem. Further, the incorporation of this fragrance composition having an enhanced diffusivity and long-lasting property of fragrance in products such as cosmetic, toiletry, bath composition, food and drink and pharmaceutical makes it possible to prepare various products having a remarkably enhanced diffusivity and long-lasting property of fragrance. Moreover, the incorporation of the compound represented by the general formula (1) together with a fragrance composition directly in various products during the preparation thereof makes it possible to prepare products having an excellent diffusivity and long-lasting property of fragrance.

While the invention has been described in detail and with reference to specific embodiments thereof, it will be apparent to one skilled in the art that various changes and modifications can be made therein without departing from the spirit and scope thereof.

This application is based on Japanese patent application No. 2000-275928 filed on Sep. 12, 2000, the entire contents thereof being hereby incorporated by reference.

What is claimed is:

1. A method for enhancing the diffusivity and long-lasting property of a fragrance, wherein the fragrance is:
    at least one carbonyl compound selected from the group consisting of 10-oxa-16-hexadecanolide, styrallyl acetate, ethyl 2,2,6-trimethylcyclohexane carboxylate and hexamethylhexahydrocyclopenta-benzopyran, which at least one carbonyl compound is the fragrance whose diffusivity and long-lasting property is enhanced, which method comprises adding (i) at least one compound selected from the group consisting of compounds represented by the general formula (1) and compounds represented by the general formula (2):

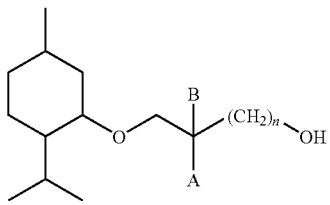
(1)

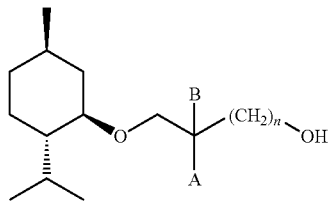
(2)

wherein A represents H or an OH group; B represents H or a methyl group; and n represents an integer of from 0 to 2, to said fragrance.

* * * * *